(12) United States Patent
Bernhardt (10) Patent No.: US 11,564,432 B2
(45) Date of Patent: Jan. 31, 2023

(54) PERSONAL PASSENGER SPACE SUPPORT DEVICE

(71) Applicant: Michael D. Bernhardt, Arvada, CO (US)

(72) Inventor: Michael D. Bernhardt, Arvada, CO (US)

(*) Notice: Subject to any disclaimer, the term of this patent is extended or adjusted under 35 U.S.C. 154(b) by 272 days.

(21) Appl. No.: 16/947,301

(22) Filed: Jul. 28, 2020

(65) Prior Publication Data

US 2021/0030090 A1 Feb. 4, 2021

Related U.S. Application Data

(60) Provisional application No. 62/881,709, filed on Aug. 1, 2019.

(51) Int. Cl.
| | | |
|---|---|---|
| *A41F 9/00* | (2006.01) | |
| *F16B 3/00* | (2006.01) | |
| *A61G 7/07* | (2006.01) | |
| *A61F 5/37* | (2006.01) | |
| *A61G 7/075* | (2006.01) | |

(52) U.S. Cl.
CPC ............. *A41F 9/002* (2013.01); *F16B 3/00* (2013.01); *A61F 5/3715* (2013.01); *A61F 5/3761* (2013.01); *A61G 7/0755* (2013.01)

(58) Field of Classification Search
CPC .......... A41F 9/002; F16B 3/00; F16B 45/008; F16B 2/08; A61F 5/3715; A61F 5/3761; A61G 7/0755
See application file for complete search history.

(56) References Cited

U.S. PATENT DOCUMENTS

| | | | | | |
|---|---|---|---|---|---|
| 1,655,092 | A | * | 1/1928 | Davis ................. | A63B 69/0059 473/212 |
| 3,423,094 | A | * | 1/1969 | Morano ............. | A63B 69/3667 473/207 |
| 4,088,326 | A | * | 5/1978 | Bifulco ............. | A63B 69/0059 473/207 |
| 4,239,228 | A | * | 12/1980 | Norman ............ | A63B 69/0059 273/DIG. 30 |
| 4,390,015 | A | * | 6/1983 | Clements ........... | A61G 7/0755 128/882 |
| 4,392,489 | A | * | 7/1983 | Wagner, Sr. ........ | A61F 5/0193 D24/190 |

(Continued)

OTHER PUBLICATIONS www.amazon.com: "Skillbuilders 30-1411 Knee Spreader with Water Resistant Cooling," downloaded from the Internet May 30, 2019.

(Continued)

*Primary Examiner* — David M Upchurch
(74) *Attorney, Agent, or Firm* — Trenner Law Firm, LLC; Mark D. Trenner (57) ABSTRACT

A personal passenger space support device is disclosed as it may be implemented to comfortably support a user's legs at a predetermined spacing in the user's own personal space while in a seated position. An example of the device includes a first leg support configured for a user's right leg, and a second leg support configured for the user's left leg. An interconnect is configured to maintain the first and second leg supports at a predetermined lateral spacing to support the user's legs apart from one another without overhanging the user's own personal space.

19 Claims, 8 Drawing Sheets

(56) References Cited

U.S. PATENT DOCUMENTS

| | | | | |
|---|---|---|---|---|
| 4,607,629 | A * | 8/1986 | Lerman | A61F 5/0193 |
| | | | | 602/24 |
| 4,706,957 | A * | 11/1987 | Jackson | A63B 69/3608 |
| | | | | 473/207 |
| 4,757,995 | A * | 7/1988 | Gallagher | A63B 69/0002 |
| | | | | 473/217 |
| 4,805,605 | A * | 2/1989 | Glassman | A61F 5/0193 |
| | | | | 128/882 |
| 4,830,366 | A * | 5/1989 | Ruden | A63B 21/028 |
| | | | | 482/122 |
| 4,889,109 | A | 12/1989 | Gifford | |
| 5,530,980 | A * | 7/1996 | Sommerhalter, Jr. | ........................ |
| | | | | A47C 20/021 |
| | | | | 5/624 |
| 5,839,978 | A * | 11/1998 | Evangelist | A63B 69/0059 |
| | | | | 128/869 |
| 5,902,189 | A * | 5/1999 | Schultz | A63B 69/0059 |
| | | | | 473/212 |
| 6,179,756 | B1 * | 1/2001 | Bertolucci | A63B 23/0488 |
| | | | | 482/131 |
| 6,332,845 | B1 * | 12/2001 | Priestley | A63B 69/0057 |
| | | | | 473/409 |
| 6,810,879 | B1 * | 11/2004 | Tinsley | A61F 5/3715 |
| | | | | 128/846 |
| 6,846,254 | B2 * | 1/2005 | Baxter | A63B 69/0059 |
| | | | | 473/450 |
| 7,166,083 | B2 * | 1/2007 | Bledsoe | A61F 5/0116 |
| | | | | 602/23 |
| 8,052,546 | B1 * | 11/2011 | Nagel | A63B 21/4019 |
| | | | | 473/422 |
| 8,556,784 | B2 * | 10/2013 | Leibowitz | A63B 21/4025 |
| | | | | 482/121 |
| D697,217 | S * | 1/2014 | Nasir | D24/190 |
| 8,814,760 | B2 * | 8/2014 | Hyacinth | A63B 21/4011 |
| | | | | 482/122 |
| 8,968,121 | B2 * | 3/2015 | Leggett | A63B 69/0002 |
| | | | | 473/422 |
| 10,086,250 | B2 * | 10/2018 | Wright | G09B 19/0038 |
| 10,869,775 | B1 * | 12/2020 | Chichetto | A61B 17/7055 |
| 2014/0060547 | A1 * | 3/2014 | Vallino | A61F 5/05858 |
| | | | | 128/845 |
| 2014/0116452 | A1 * | 5/2014 | Ingimundarson | A61F 5/3715 |
| | | | | 128/882 |

OTHER PUBLICATIONS www.amazon.com: "Rolyan Abductor, Leg and Knee Separator for Sitting or Supine Position, Dial Adjusts to Patient Specific Amount of Hip Abduction and ROM for Hip Injury and Surgery Recovery and Rehabilitation," downloaded from the Internet May 30, 2019.

www.amazon.com: "Rolyan Pediatric Knee Separator, Soft Block for Keeping Knees apart and Holding Hips in Abduction, Aid for Distributing Pressure Over Thighs, Contoured to Support and Comfort Legs and Hips," downloaded from the internet May 30, 2019.

* cited by examiner

PERSONAL PASSENGER SPACE SUPPORT DEVICE

PRIORITY CLAIM

This application claims the priority benefit of U.S. Provisional Patent Application No. 62/881,709 filed Aug. 1, 2019 for "Personal Passenger Space Support Device of Michael D. Bernhardt, incorporated by reference for all that is disclosed as though fully set forth herein.

BACKGROUND

In tight seating spaces that exist in many public places (e.g., airplanes, stadiums, buses, trains, etc.), an effort is needed to keep one's personal space regarding their legs. The tendency is often to relax and let the legs "rest" (laterally) against something. In many situations, that "something" is actually "someone". This is especially evident in longer-lasting situations such as air travel. The only solution currently available is self muscle control. This can result in fatigue, discomfort, and perhaps even leg and/or back pain. Indeed, if you already have leg and/or back pain, it may not be possible to exert sufficient muscle control to maintain your personal space.

DETAILED DESCRIPTION

A personal passenger space support device is disclosed. In an example, the device is a lateral knee or leg rest that enables the user to relax their legs without having to exert muscle force to hold their legs in place, and even in this relaxed status, prevent the user's legs from opening or widening such that the user's legs might extend beyond the user's own personal space and potentially impede upon the personal space of those sitting alongside.

An example personal passenger space support device includes two "J" brackets connected by an adjustable feature for sizing (laterally). The round part of the "J" shaped portion of each bracket cradles one leg. The straight portions of each bracket adjustably connect to each other, allowing for a proper, comfortable, and space-respecting fit.

The device can be broken down and stored more easily when not in use. This breakdown feature also promotes safety, e.g., in case the user must move quickly to exit their seat.

Before continuing, it is noted that as used herein, the terms "includes" and "including" mean, but is not limited to, "includes" or "including" and "includes at least" or "including at least" The term "based on" means "based on" and "based at least in part on."

It is also noted that the term "personal space" is used herein to have a specific meaning. That is, personal space is not limited to specific dimensions but can be readily defined by the user (and/or other people near the user). By way of illustration, a user's personal space is typically well defined in public seating areas, such as in passenger seating on buses, airplanes, waiting rooms, etc. While typically not defined by a provided border, it is generally accepted that a user's personal space should not extend into the adjacent seating area(s). Indeed, the user's personal space typically includes a buffer zone so that the user's legs do not touch the person sitting next to them or cause the person sitting next to them to have to move or withdraw into their own seating area to avoid touching the person next to them. As such, personal space has a very specific, definable meaning, even though the specific dimensions may vary based on the type of seating, the user's own personal preference (and those seated adjacent the user), and can readily be ascertained on a situation-specific basis.

Figure 1:
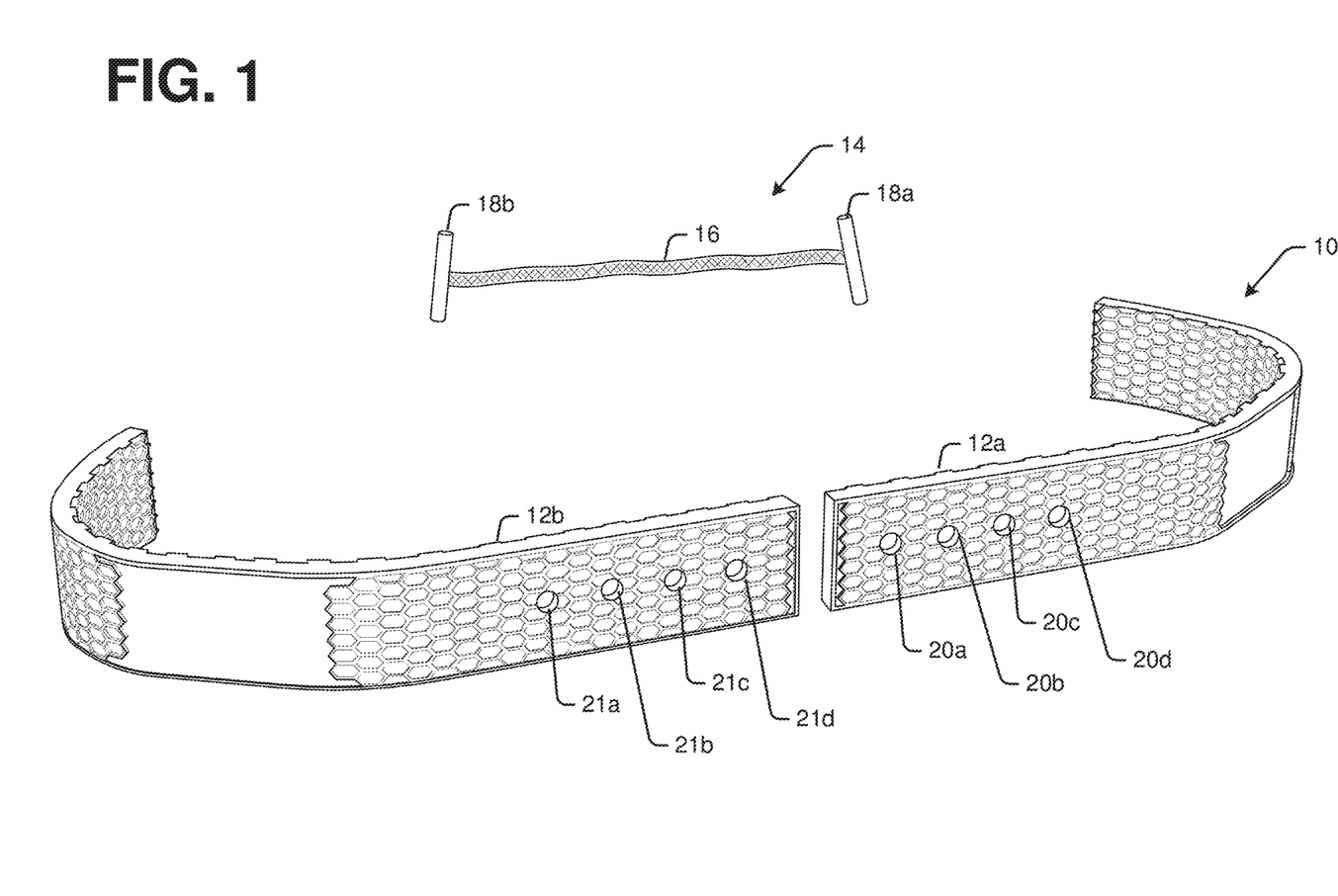
FIG. 1 is a perspective view of an example personal passenger space support device.
Figure 2:
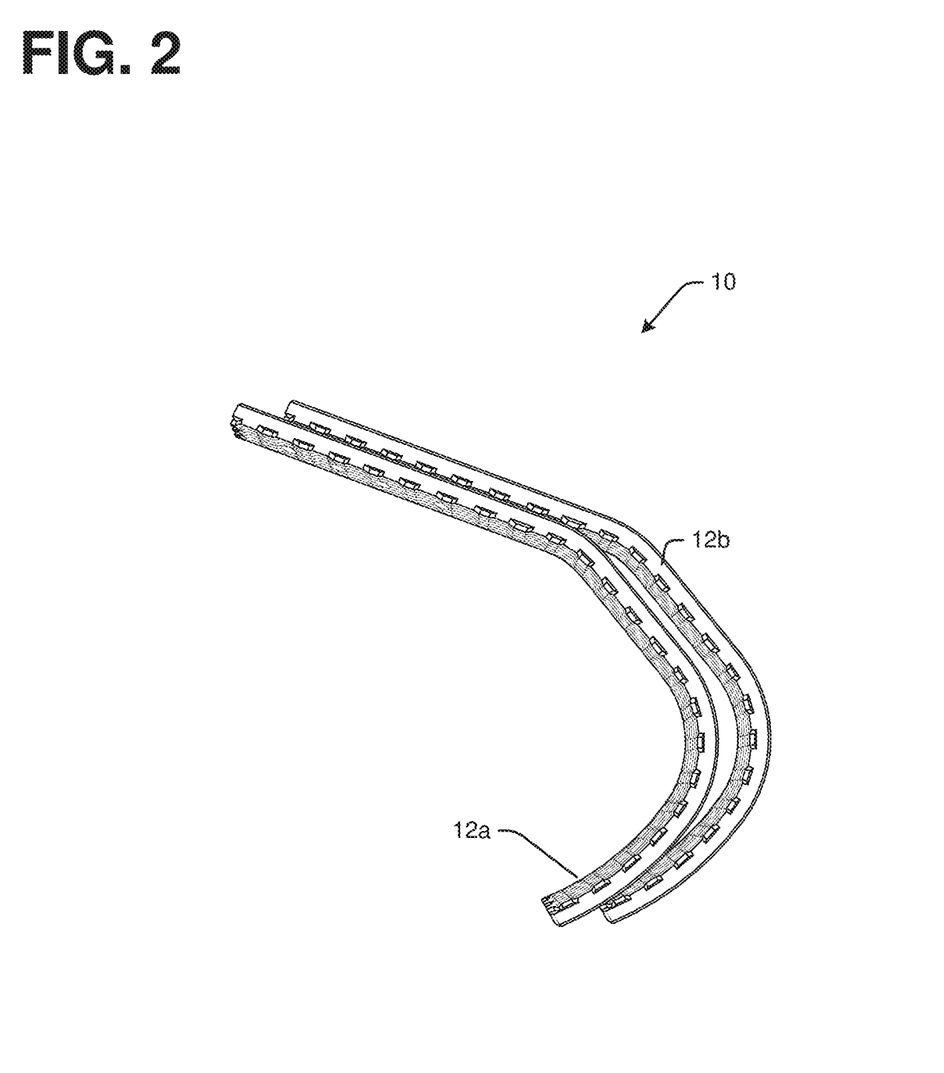
FIG. 2 is a perspective view of the example personal passenger space support device of FIG. 1 in a collapsed configuration.
Figure 3:
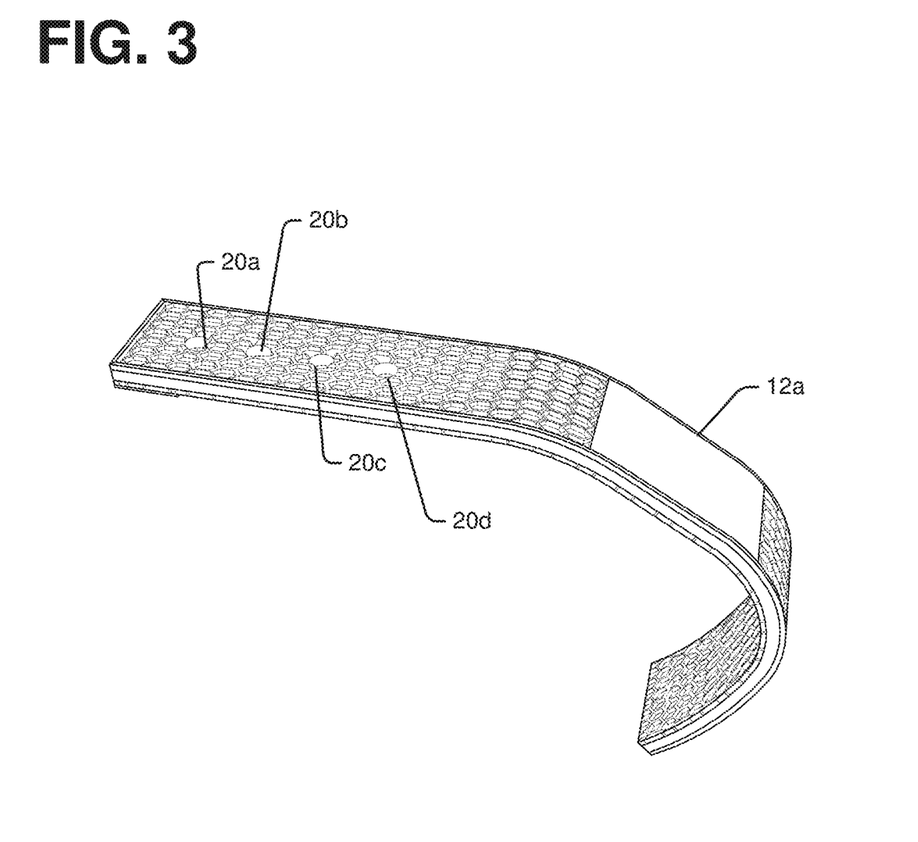
FIG. 3 is a perspective view of one of the leg supports of the example personal passenger space support device of FIG. 1.

FIG. 1 is a perspective view of an example personal passenger space support device 10. FIG. 2 is a perspective view of the example personal passenger space support device 10 of FIG. 1 in a collapsed configuration (e.g., for storage). FIG. 3 is a perspective view of one of the leg supports 12a, 12b of the example personal passenger space support device 10 of FIG. 1.

An example personal passenger space support device 10 enables a user to comfortably support the user's legs at a predetermined lateral spacing so that the user's legs remain in the user's own personal space when the user is in a seated position. An example of the device includes a first leg support 12a configured for a user's right leg, and a second leg support 12b configured for the user's left leg. An interconnect 14 is configured to maintain the first and second leg supports 12a, 12b at a predetermined lateral spacing to support the user's legs apart from one another without overhanging the user's own personal space (e.g., into someone else's personal space).

In an example, the first and second leg supports 12a, 12b include substantially "J" shaped brackets connected by the interconnect 14. A round portion of each of the "J" shaped brackets is shaped to cradle each of the legs of the user. A flat portion of each of the "J" shaped brackets crosses between the user's legs.

In an example, the first and second leg supports 12a, 12b are manufactured of a plastic or composite material (e.g., carbon fiber) that provides suitable strength while still being lightweight. The first and second leg supports 12a, 12b may also include a honeycomb, to further provide strength while being lightweight for easy transport. This configuration also serves as an advantage over a flat surface for comfort (e.g., less leg-surface contact, sweating, marking, etc.). However, the device is not limited to any specific type or configuration of the material of manufacture.

In an example, the interconnect 14 secures the first and second leg supports so that the user can exert lateral force against the brackets without compromising the predetermined lateral spacing. The predetermined spacing is user-adjustable via the interconnect 14.

In an example, the curved or rounded portion of the "J" shaped leg supports cradle the user's legs. The curved portion of the "J" may have a diameter of about 7 inches. However, larger sizes may be provided for larger users, and smaller sizes may be provided for children or smaller users.

In an example, the leg supports are configured for a proper, comfortable, and space-respecting fit. The distance of the space between the user's leg may be adjusted. It is noted that the device 10 is configured, not to hold the user's legs apart, but the opposite, that is, to keep the legs comfortably within the user's personal space.

In an example, the device 10 is comfortable (e.g., having a wide, flat surface), light-weight, and enables the user to exert lateral force by his or her legs without compromising the personally adjusted limit.

In an example, the device 10 is designed not only for comfort, but for safety as well. The "J" feature does not loop entirely around the user's leg(s) and thus serves the intentional purpose of allowing the user to remove the device rapidly and easily if the user must move quickly to exit the seat.

In an example, the brackets can be unassembled to be stored more easily when not in use. In an example, the device 10 has a flexible connector (e.g., a hook and loop strap) to allow the two separate leg supports to be configured in a single item that can be readily carried and/or stowed when not in use.

In an example, the device 10 is configured so that there is no blockage between the user's legs. This results in comfort during use, and the ability of the user to reach items on the floor between the user's feet.

Figure 4:
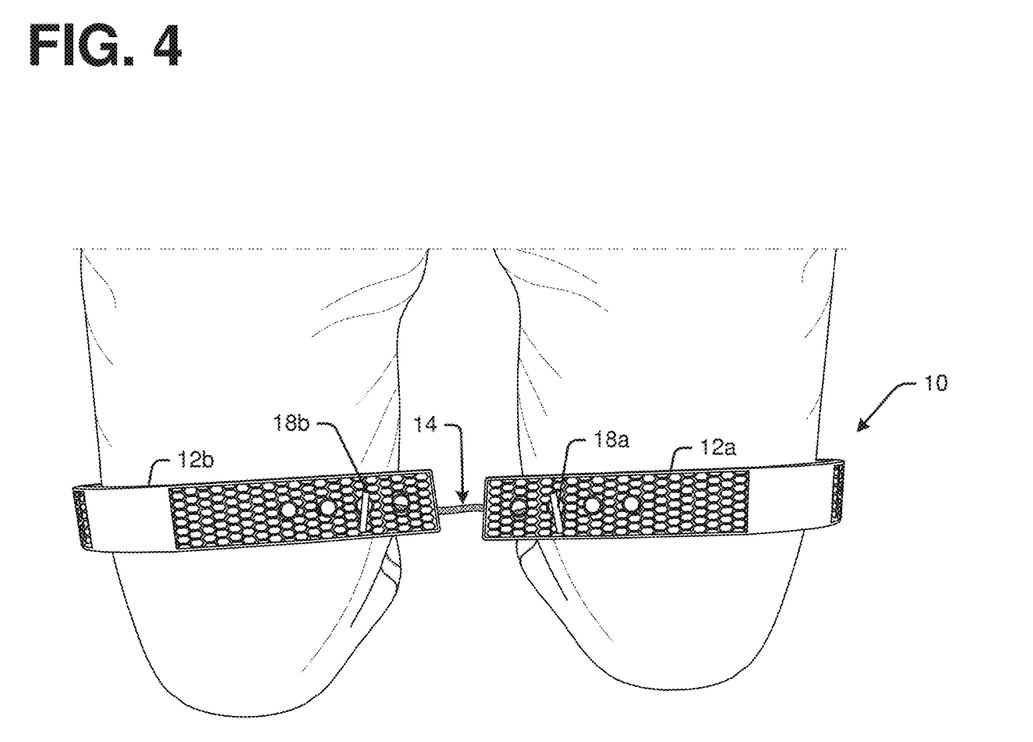
FIG. 4 is a perspective view of an example personal passenger space support device shown as it may be used to support a user's legs in a seated position.

FIG. 4 is a perspective view of an example personal passenger space support device shown as it may be used to support a user's legs in a seated position. In an example, the first and second leg supports 12a, 12b are configured with nothing between the user's legs when in use.

The interconnect 14 may have any of a variety of configurations to enable various end-use scenarios. For example, the interconnect 14 may be stretchable (e.g., elastic band), providing the user with some give and more comfort. The stretchable allowance may be sufficiently small such that the user enjoys some flexibility while maintaining the ability to stay within the user's personal space. In another example, the interconnect 14 does not stretch (e.g., a strap).

In another example, the interconnect 14 is rigid. For example, the interconnect 14 may be a rod for more durability. In yet another example, the interconnect is flexible. For example, the interconnect 14 may be a rope for easy transport and storage.

In the example shown in FIGS. 1 and 4, the interconnect 14 is formed by a cord 16 having T-connectors 18a, 18b on each end of the cord 16. The cord attaches on one end of the cord 16 through openings 20a-d formed through the first leg support 12a, and the cord attaches on the other end through openings 21a-d on the second leg support 12b. The cord is held in position by the T-connectors, thereby fastening the leg supports 12a, 12b at the predetermined distance. The distance can be adjusted, e.g., by selecting different openings 20a-d and/or 21a-d and/or by varying the length of the cord 16.

Other types of interconnects are also possible. By way of illustration, an example interconnect may include a strap (not shown) that fits between slots in each of the leg supports.

Before continuing, it should be noted that the examples described above are provided for purposes of illustration, and are not intended to be limiting. Other devices and/or device configurations may be utilized to carry out the operations described herein.

In addition, the operations shown and described are provided to illustrate example implementations. Still other operations may also be implemented.

Figure 5:
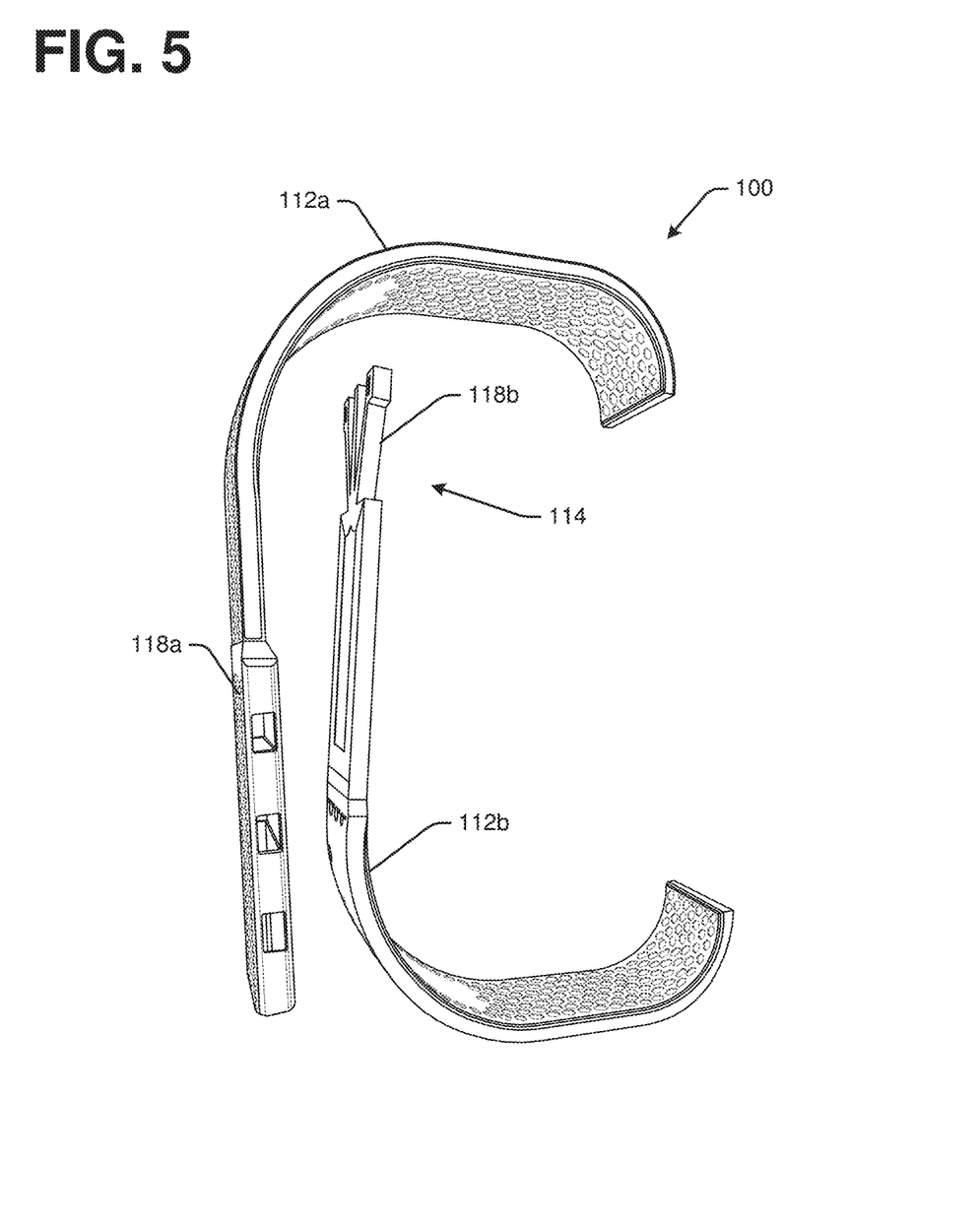
FIG. 5 is a perspective view of another example personal passenger space support device.
Figure 6:
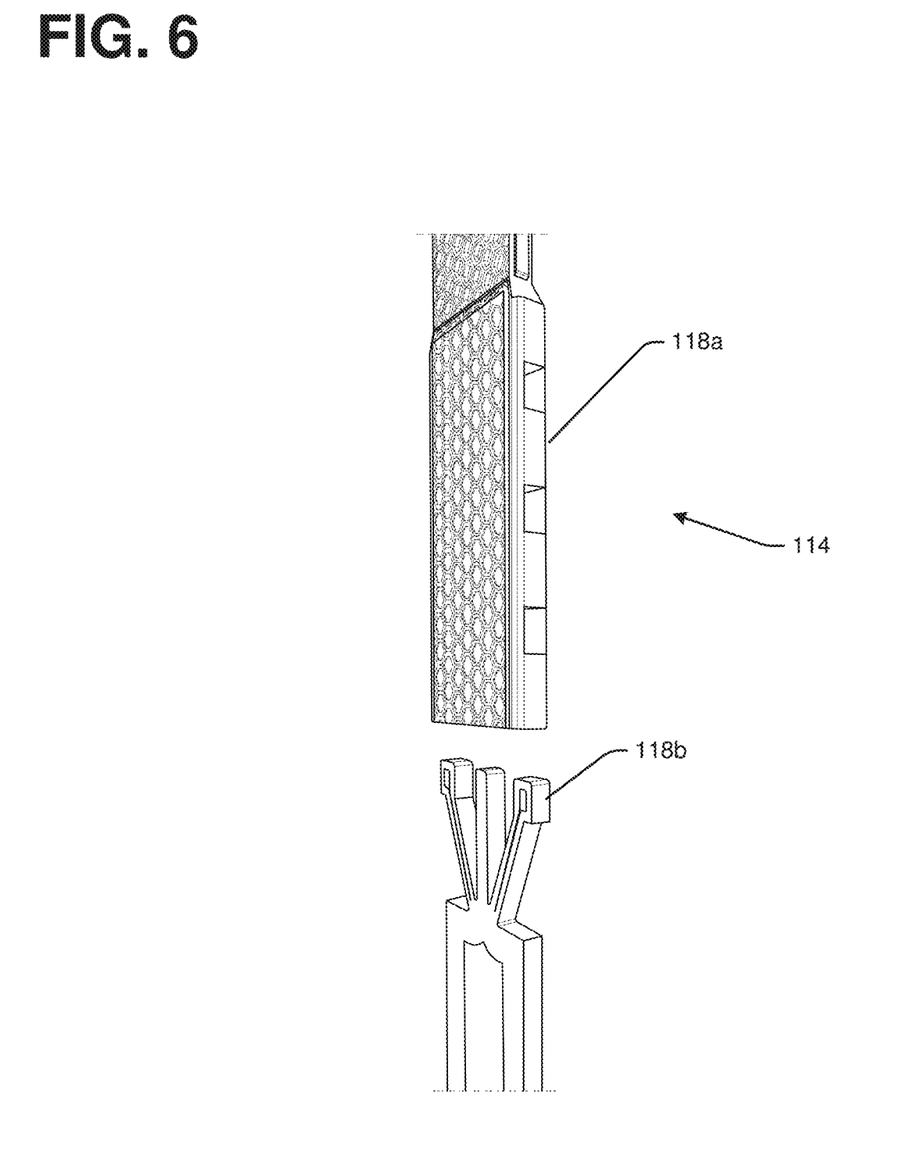
FIG. 6 is a close-up view of an example connection mechanism of the personal passenger space support device of FIG. 5.
Figure 7:
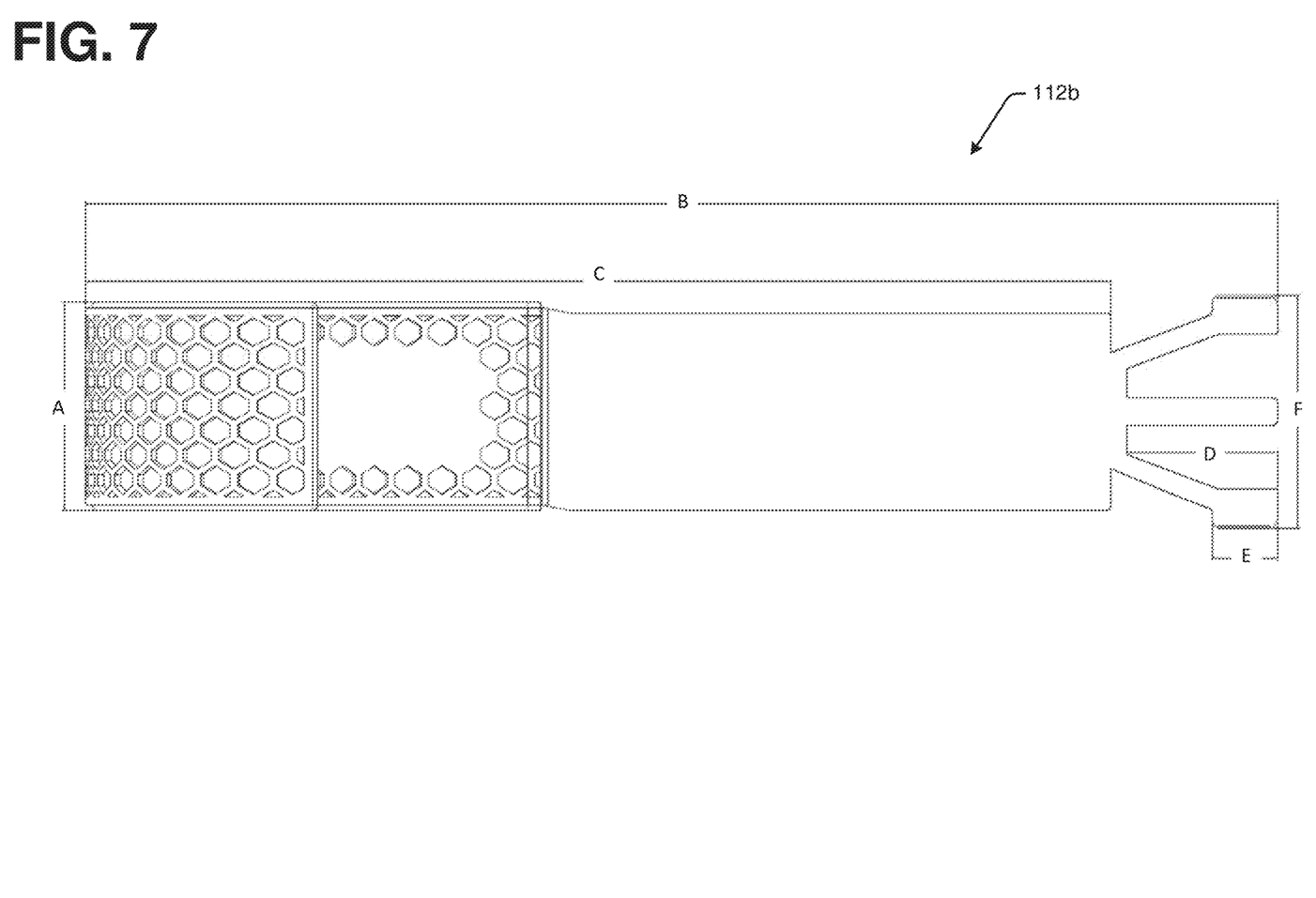
FIG. 7 is a top view of one of the leg supports of the example personal passenger space support device of FIG. 5.

FIG. 5 is a perspective view of another example personal passenger space support device 100. FIG. 6 is a close-up view of an example connection mechanism 114 of the personal passenger space support device 110 of FIG. 5. FIG. 7 is a top view of one of the leg supports 112b of the example personal passenger space support device 110 of FIG. 5.

In the example shown in FIGS. 5-8a and 8b, the interconnect 114 is formed by a buckle. The buckle has a first connector 118a formed as part of the first leg support 112a. The buckle has a second connector 118b formed as part of the second leg support 112b. The first connector 118a mates with the second connector 118b to form a secure connection therebetween, which can be released by pressing the sides of the second connector 118b so that the second connector 118b slides out of the side openings in the first connector 118a. In an example, the buckle has a plurality of adjustments (e.g., side openings in the first connector 118a) to make the predetermined spacing user-adjustable by selection of various of the adjustments (e.g., the side openings).

Figure 8A:
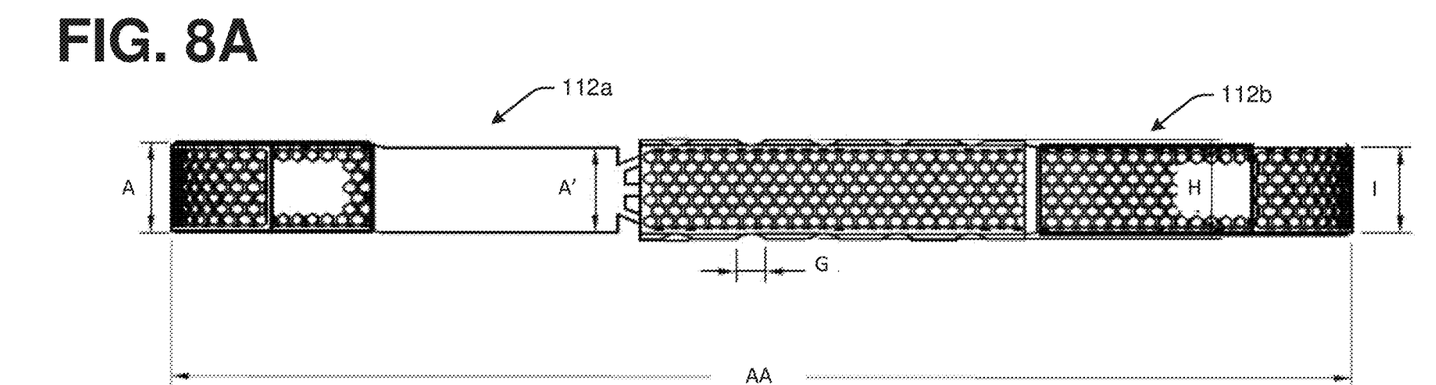
FIG. 8A is a top view of the example personal passenger space support device of FIG. 5.
Figure 8B:
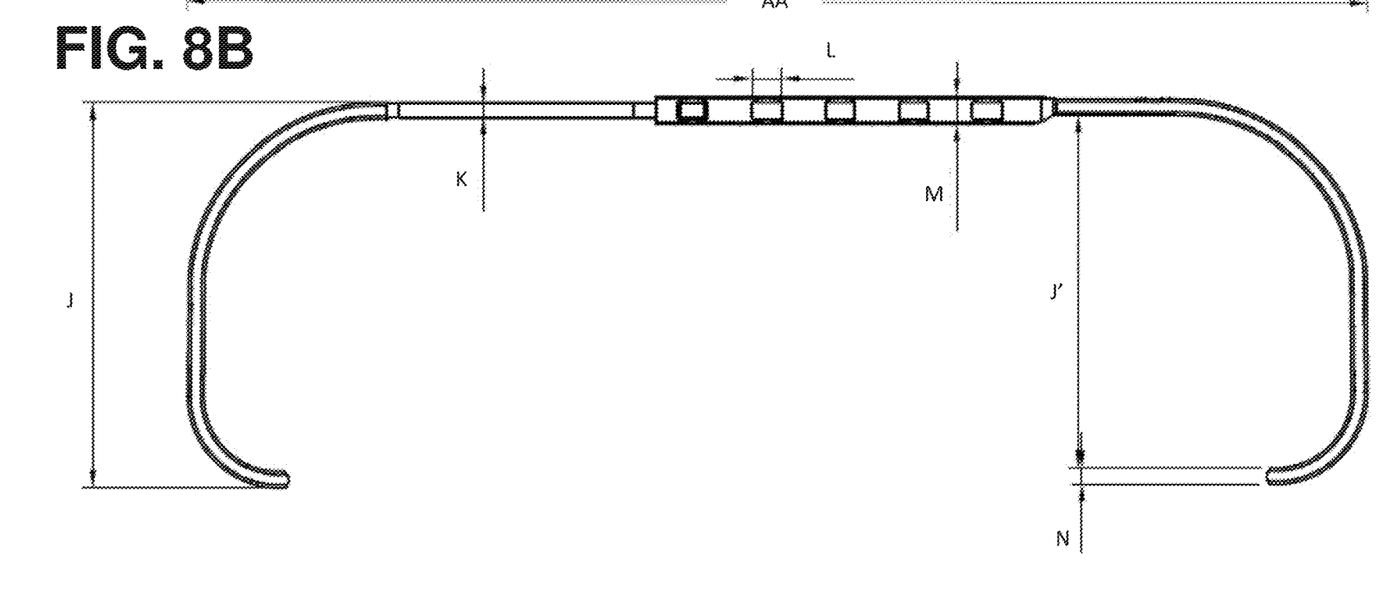
FIG. 8B is a side view of the example personal passenger space support device corresponding to FIG. 8A.

FIG. 8A is a top view of the example personal passenger space support device 110 of FIG. 5. FIG. 8B is a side view of the example personal passenger space support device 110 corresponding to FIG. 8A. Example dimensions are given in the table below for purposes of non-limiting illustration.

| Figure Label | Dimension (mm) |
|---|---|
| A | 37 |
| AA | 481.94 |
| A' | 35 |
| B | 212.2 |
| C | 182.5 |
| D | 26.85 |
| E | 11.66 |
| F | 41.31 |
| G | 12 |
| H | 40.5 |
| I | 35 |
| J | 156.9 |
| J' | 43.55 |
| K | 5.74 |
| L | 12 |
| M | 11.46 |
| N | 65 |

Other dimensions are also contemplated, as will be readily understood by those having ordinary skill in the art after becoming familiar with the teachings herein.

It is noted that the examples shown and described are provided for purposes of illustration and are not intended to be limiting. Still other examples are also contemplated.

The invention claimed is:

1. A personal passenger space leg support device to comfortably support a user's legs in a predetermined lateral spacing of the user's own personal space while in a seated position, comprising:
   a first leg support having a first elongated section extending into a first substantially J-shaped end portion configured to wrap only partly around the user's right leg;

a second leg support having a second elongated section extending into a second substantially J-shaped end portion configured to wrap only partly around the user's left leg; and an interconnect connecting between the first and second elongated sections of the first and second leg supports, the interconnect configured to hold the first and second leg supports together against a force exerted by the user's legs against the first and second substantially J-shaped end portions so that the user's legs are kept from moving beyond the predetermined lateral spacing and do not overhang from the user's own personal space.

2. The device of claim 1, wherein the predetermined lateral spacing is user-adjustable via the interconnect.

3. The device of claim 1, further comprising a round portion of each of the J-shaped end portion, the round portion shaped to cradle the legs of the user.

4. The device of claim 1, further comprising a flat portion of the first and second elongated sections.

5. The device of claim 1, wherein the interconnect secures the first and second leg supports so that the user can exert lateral force against the J-shaped end portions without compromising the predetermined lateral spacing.

6. The device of claim 1, wherein the first and second leg supports are configured to be disconnected and stored together in a collapsed configuration.

7. The device of claim 1, wherein the first and second leg supports are configured with nothing between the user's legs when in use.

8. The device of claim 1, wherein the interconnect is stretchable.

9. The device of claim 1, wherein the interconnect does not stretch.

10. The device of claim 1, wherein the interconnect is rigid.

11. The device of claim 1, wherein the interconnect is flexible.

12. The device of claim 1, wherein the interconnect is formed by a cord having T-connectors on each end of the cord, the cord attaching on each end of the cord through openings formed in each of the first and second leg supports and held in position by the T-connectors.

13. The device of claim 12, further comprising a plurality of the openings formed in each of the first and second leg supports to make the predetermined spacing user-adjustable by connecting the cord to one of the openings on each of the first and second leg supports.

14. The device of claim 1, wherein the interconnect is formed by buckle.

15. The device of claim 14, wherein the buckle has a first connector formed as part of the first leg support, and the buckle has a second connector formed as part of the second leg support, the first connector mating with the second connector.

16. The device of claim 14, wherein the buckle has a plurality of adjustments to make the predetermined spacing user-adjustable by selection of various of the adjustments.

17. A personal passenger space leg support device to comfortably support a user's legs in the user's own personal space while in a seated position, comprising:

a first leg support having a first elongated section terminating in a first substantially J-shaped end portion configured to wrap only partly around the user's right leg;

a second leg support having a second elongated section terminating in a second substantially J-shaped end portion configured to wrap only partly around the user's left leg; and a user-adjustable interconnect connecting between the first and second elongated sections of the first and second leg supports, the user-adjustable interconnect configured to keep the first and second leg supports from extending beyond a predetermined leg spacing against a force exerted by the user's legs to prevent the user's legs from overhanging the user's own personal space.

18. The device of claim 17, further comprising a round portion of each of the J-shaped end portions to cradle each of the legs of the user.

19. A personal passenger space leg support device to comfortably support a user's legs at a user-selectable spacing in the user's own personal space while in a seated position, comprising:

a first leg support configured for a user's right leg;

a second leg support configured for the user's left leg; and a cord interconnection having T-connectors on each end;

a plurality of openings formed in each of the first and second leg supports to receive the T-connectors, one of the plurality of openings on each of the first and second leg supports selected by the user to define the user-selectable spacing;

wherein the cord interconnection secures the first and second leg supports together so that the user can exert lateral force against the first and second leg supports without compromising the user-selectable spacing.

* * * * *